US011337750B2

(12) United States Patent
Pappone et al.

(10) Patent No.: US 11,337,750 B2
(45) Date of Patent: *May 24, 2022

(54) ABLATION CATHETER WITH FLEXIBLE ELECTRODE

(71) Applicant: ST. JUDE MEDICAL, ATRIAL FIBRILLATION DIVISION, INC., St. Paul, MN (US)

(72) Inventors: Carlo Pappone, Lecco (IT); Alan de la Rama, Cerritos, CA (US); Peter C. Chen, Irvine, CA (US); Cary Hata, Irvine, CA (US); Jared A. Shimizu, Irvine, CA (US)

(73) Assignee: ST. JUDE MEDICAL, ATRIAL FIBRILLATION DIVISION, INC., St. Paul, MN (US)

( * ) Notice: Subject to any disclaimer, the term of this patent is extended or adjusted under 35 U.S.C. 154(b) by 827 days.

This patent is subject to a terminal disclaimer.

(21) Appl. No.: 16/224,172

(22) Filed: Dec. 18, 2018

(65) Prior Publication Data

US 2019/0192221 A1    Jun. 27, 2019

Related U.S. Application Data

(63) Continuation of application No. 15/348,823, filed on Nov. 10, 2016, now Pat. No. 10,188,459, which is a
(Continued)

(51) Int. Cl.
*A61B 18/12* (2006.01)
*A61B 18/14* (2006.01)
(Continued)

(52) U.S. Cl.
CPC .......... *A61B 18/1492* (2013.01); *A61B 90/06* (2016.02); *A61B 2017/00867* (2013.01);
(Continued)

(58) Field of Classification Search
CPC ...... A61B 18/1492; A61B 2018/00023; A61B 2018/00029; A61B 2018/00351;
(Continued)

(56) References Cited

U.S. PATENT DOCUMENTS

| 4,325,374 A | 4/1982 | Komiya |
| 5,163,005 A | 11/1992 | Greene et al. |

(Continued)

FOREIGN PATENT DOCUMENTS

| EP | 109178 B2 | 1/2000 |
| WO | 1996034652 A1 | 11/1996 |

(Continued)

OTHER PUBLICATIONS

PCT International Search Report for PCT/US2008/069248, dated Jan. 15, 2009, 2 pages.
(Continued)

*Primary Examiner* — Daniel W Fowler
(74) *Attorney, Agent, or Firm* — Armstrong Teasdale LLP

(57) ABSTRACT

A flexible tip electrode for an ablation catheter is disclosed. The catheter includes a catheter body and a hollow elongate tip electrode disposed at a distal end of the catheter body. The electrode includes a sidewall provided with one or more elongate gaps extending therethrough. The one or more elongate gaps providing flexibility in the sidewall for bending movement of the tip electrode relative to a longitudinal axis of the catheter body.

25 Claims, 15 Drawing Sheets

Related U.S. Application Data continuation of application No. 14/313,837, filed on Jun. 24, 2014, now Pat. No. 9,510,903, which is a continuation of application No. 13/910,771, filed on Jun. 5, 2013, now Pat. No. 8,790,341, which is a continuation of application No. 13/481,848, filed on May 27, 2012, now Pat. No. 8,480,669, which is a continuation of application No. 11/853,759, filed on Sep. 11, 2007, now Pat. No. 8,187,267.

(60) Provisional application No. 60/939,799, filed on May 23, 2007.

(51) Int. Cl.
*A61B 90/00* (2016.01)
*A61B 17/00* (2006.01)
*A61B 18/00* (2006.01)

(52) U.S. Cl.
CPC ............... *A61B 2018/00023* (2013.01); *A61B 2018/00029* (2013.01); *A61B 2018/00148* (2013.01); *A61B 2018/00154* (2013.01); *A61B 2018/00351* (2013.01); *A61B 2018/00357* (2013.01); *A61B 2018/00839* (2013.01); *A61B 2018/1465* (2013.01); *A61B 2018/1475* (2013.01); *A61B 2090/064* (2016.02); *A61B 2090/065* (2016.02); *A61B 2218/002* (2013.01); *C08L 2201/12* (2013.01)

(58) Field of Classification Search
CPC .. A61B 2018/00839; A61B 2018/1465; A61B 2018/1475
See application file for complete search history.

(56) References Cited

U.S. PATENT DOCUMENTS

| | | |
|---|---|---|
| 5,279,299 A | 1/1994 | Imran |
| 5,378,230 A | 1/1995 | Mahurkar |
| 5,462,521 A | 10/1995 | Brucker et al. |
| 5,487,385 A | 1/1996 | Avitall |
| 5,520,682 A | 5/1996 | Baust et al. |
| 5,545,200 A | 8/1996 | West et al. |
| 5,681,280 A | 10/1997 | Rusk et al. |
| 5,688,267 A | 11/1997 | Panescu et al. |
| 5,800,428 A | 9/1998 | Nelson et al. |
| 5,833,632 A | 11/1998 | Jacobsen et al. |
| 5,902,328 A | 5/1999 | Lafontaine et al. |
| 5,919,188 A | 7/1999 | Shearon et al. |
| 5,951,471 A | 9/1999 | de la Rama et al. |
| 5,992,418 A | 11/1999 | de la Rama et al. |
| 6,001,005 A | 12/1999 | Anderson, III et al. |
| 6,003,080 A | 12/1999 | Ratcliff et al. |
| 6,017,338 A | 1/2000 | Brucker et al. |
| 6,030,382 A | 2/2000 | Fleischman et al. |
| 6,053,912 A | 4/2000 | Panescu et al. |
| 6,210,400 B1 | 4/2001 | Hebert et al. |
| 6,217,573 B1 | 4/2001 | Webster |
| 6,235,022 B1 | 5/2001 | Hallock et al. |
| 6,251,134 B1 | 6/2001 | Alt et al. |
| 6,273,876 B1 | 8/2001 | Klima et al. |
| 6,356,790 B1 | 3/2002 | Maguire et al. |
| 6,385,472 B1 | 5/2002 | Hall et al. |
| 6,464,632 B1 | 10/2002 | Taylor |
| 6,493,590 B1 | 12/2002 | Wessman et al. |
| 6,522,930 B1 | 2/2003 | Schaer et al. |
| 6,604,003 B2 | 8/2003 | Fredricks et al. |
| 6,611,699 B2 | 8/2003 | Messing |
| 6,662,034 B2 | 12/2003 | Segner et al. |
| 6,780,183 B2 | 8/2004 | Jimenez et al. |
| 6,921,397 B2 | 7/2005 | Corcoran et al. |
| 6,980,843 B2 | 12/2005 | Eng et al. |
| 7,137,395 B2 | 11/2006 | Fried et al. |
| 7,389,148 B1 | 6/2008 | Morgan |
| 7,815,635 B2 | 10/2010 | Wittkampf et al. |
| 7,824,406 B2 | 11/2010 | Wang et al. |
| 7,857,810 B2 | 12/2010 | Wang et al. |
| 7,873,401 B2 | 1/2011 | Shachar |
| 8,048,072 B2 | 11/2011 | Verin et al. |
| 2001/0012956 A1 | 8/2001 | Behl et al. |
| 2002/0058866 A1 | 5/2002 | Segner et al. |
| 2002/0103426 A1 | 8/2002 | Segner et al. |
| 2002/0156420 A1 | 10/2002 | Anderson et al. |
| 2003/0088244 A1 | 5/2003 | Swanson et al. |
| 2003/0125730 A1 | 7/2003 | Berube et al. |
| 2004/0015215 A1 | 1/2004 | Fredricks et al. |
| 2004/0153056 A1 | 8/2004 | Muller et al. |
| 2004/0181138 A1 | 9/2004 | Hindricks et al. |
| 2004/0204671 A1 | 10/2004 | Stubbs et al. |
| 2004/0231683 A1 | 11/2004 | Eng et al. |
| 2004/0236350 A1 | 11/2004 | Lewis et al. |
| 2004/0243143 A1 | 12/2004 | Corcoran et al. |
| 2004/0267106 A1 | 12/2004 | Segner et al. |
| 2005/0004563 A1 | 1/2005 | Racz et al. |
| 2005/0049583 A1 | 3/2005 | Swanson |
| 2005/0054989 A1 | 3/2005 | McGuckin et al. |
| 2005/0070894 A1 | 3/2005 | McClurken |
| 2005/0096647 A1 | 5/2005 | Steinke et al. |
| 2005/0187561 A1 | 8/2005 | Lee-Sepsick et al. |
| 2005/0197633 A1 | 9/2005 | Schwartz et al. |
| 2005/0272975 A1 | 12/2005 | McWeeney et al. |
| 2006/0004353 A1 | 1/2006 | Koyfman et al. |
| 2006/0064123 A1 | 3/2006 | Bonnette et al. |
| 2006/0149192 A1 | 7/2006 | Deniega et al. |
| 2006/0200191 A1 | 9/2006 | Zadno-Azizi |
| 2006/0278246 A1 | 12/2006 | Eng et al. |
| 2006/0287650 A1 | 12/2006 | Cao et al. |
| 2007/0021743 A1 | 1/2007 | Rioux et al. |
| 2007/0060847 A1 | 3/2007 | Leo et al. |
| 2007/0073288 A1 | 3/2007 | Hall et al. |
| 2007/0270791 A1 | 11/2007 | Wang et al. |
| 2008/0091193 A1 | 4/2008 | Kauphusman et al. |
| 2008/0161789 A1 | 7/2008 | Thao et al. |
| 2008/0249522 A1 | 10/2008 | Pappone et al. |
| 2008/0275428 A1 | 11/2008 | Tegg et al. |
| 2008/0294158 A1 | 11/2008 | Pappone et al. |
| 2009/0012517 A1 | 1/2009 | de la Rama et al. |
| 2009/0018497 A1 | 1/2009 | Birchard et al. |
| 2010/0004632 A1 | 1/2010 | Wu et al. |
| 2010/0174177 A1 | 7/2010 | Wu |
| 2011/0118582 A1 | 5/2011 | De La Rama et al. |
| 2012/0255130 A1 | 10/2012 | Bazito et al. |

FOREIGN PATENT DOCUMENTS

| | | |
|---|---|---|
| WO | 2003049631 A1 | 6/2003 |
| WO | 2005048858 A1 | 6/2005 |
| WO | 2005094661 A1 | 10/2005 |
| WO | 2007015139 A3 | 4/2007 |
| WO | 2008010039 A1 | 1/2008 |

OTHER PUBLICATIONS

International Search Report and Written Opinion for PCT/US2011/027907, dated May 13, 2011, 9 pages.
International Search Report and Written Opinion for PCT/US2010/049836, dated Nov. 15, 2010, 9 pages.
Supplementary European Search Report for EP Application No. 08827495.6-2305, dated May 29, 2010, 8 pages.

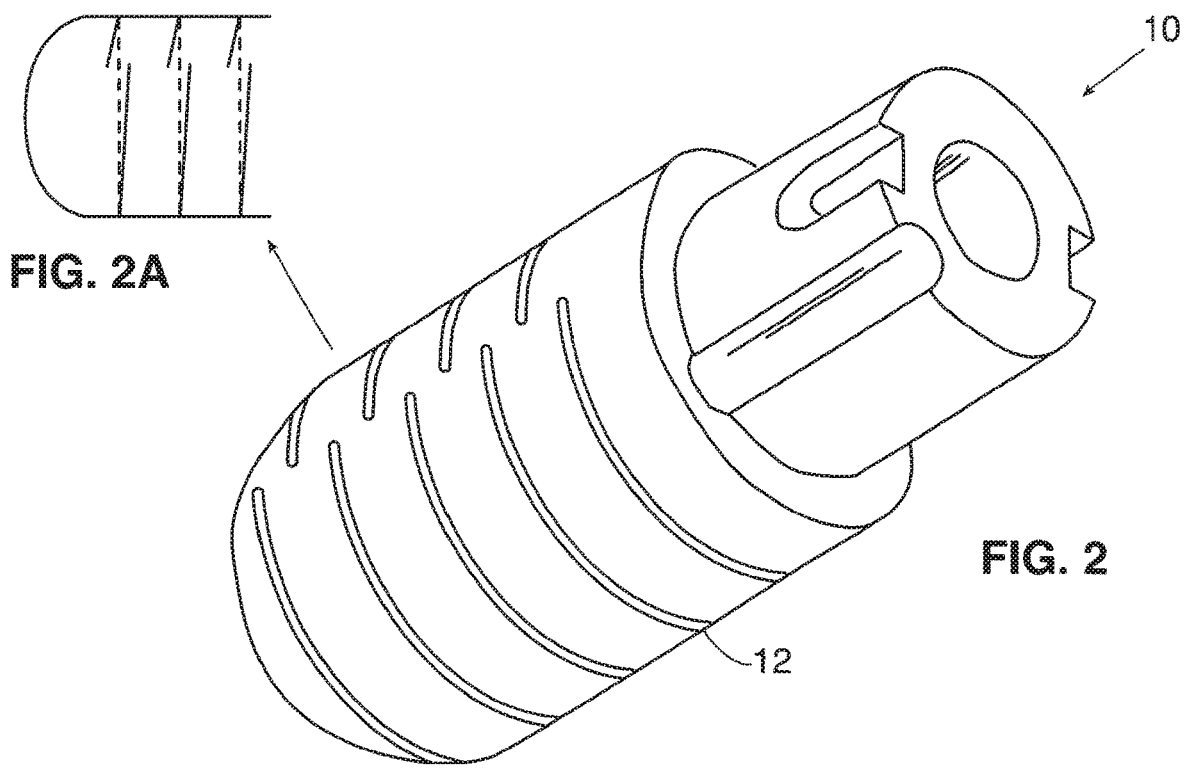
FIG. 2A
FIG. 2
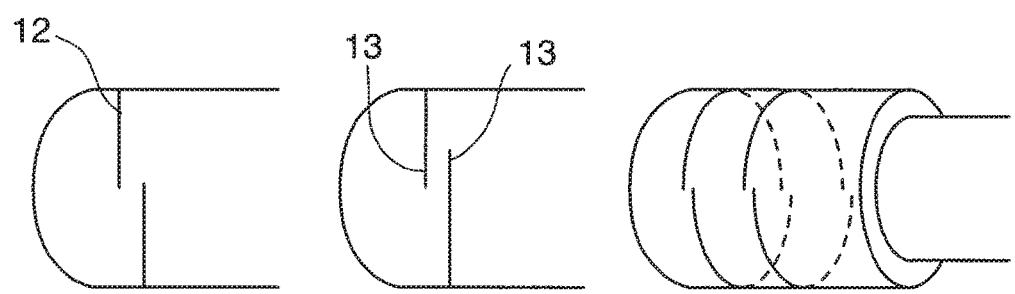
FIG. 2B    FIG. 2C    FIG. 2D

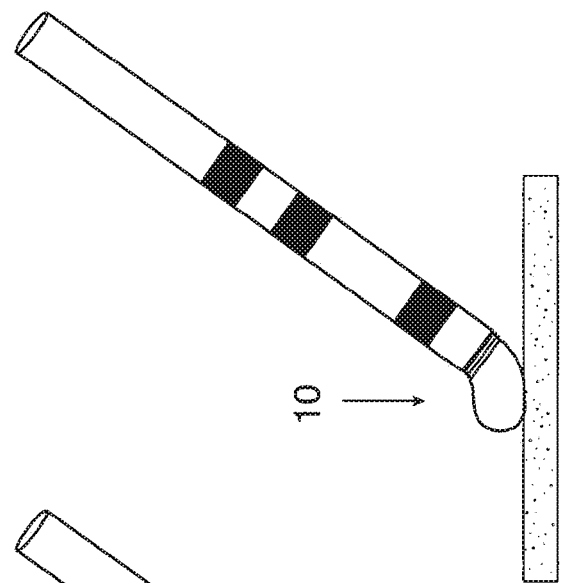
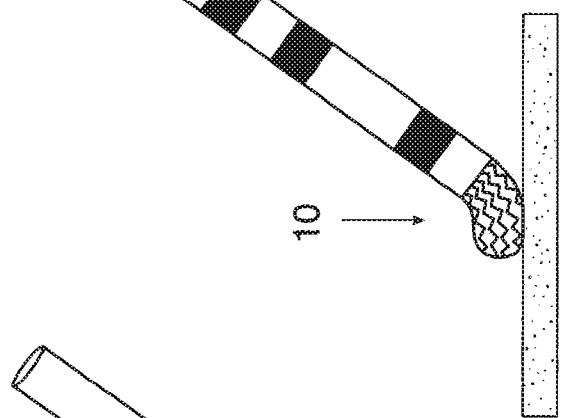
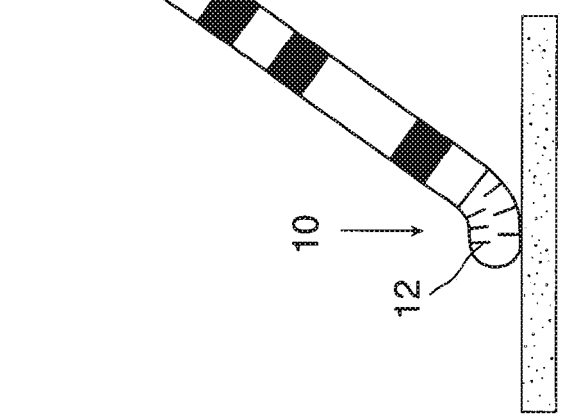
FIG. 7A
FIG. 7B
FIG. 7C

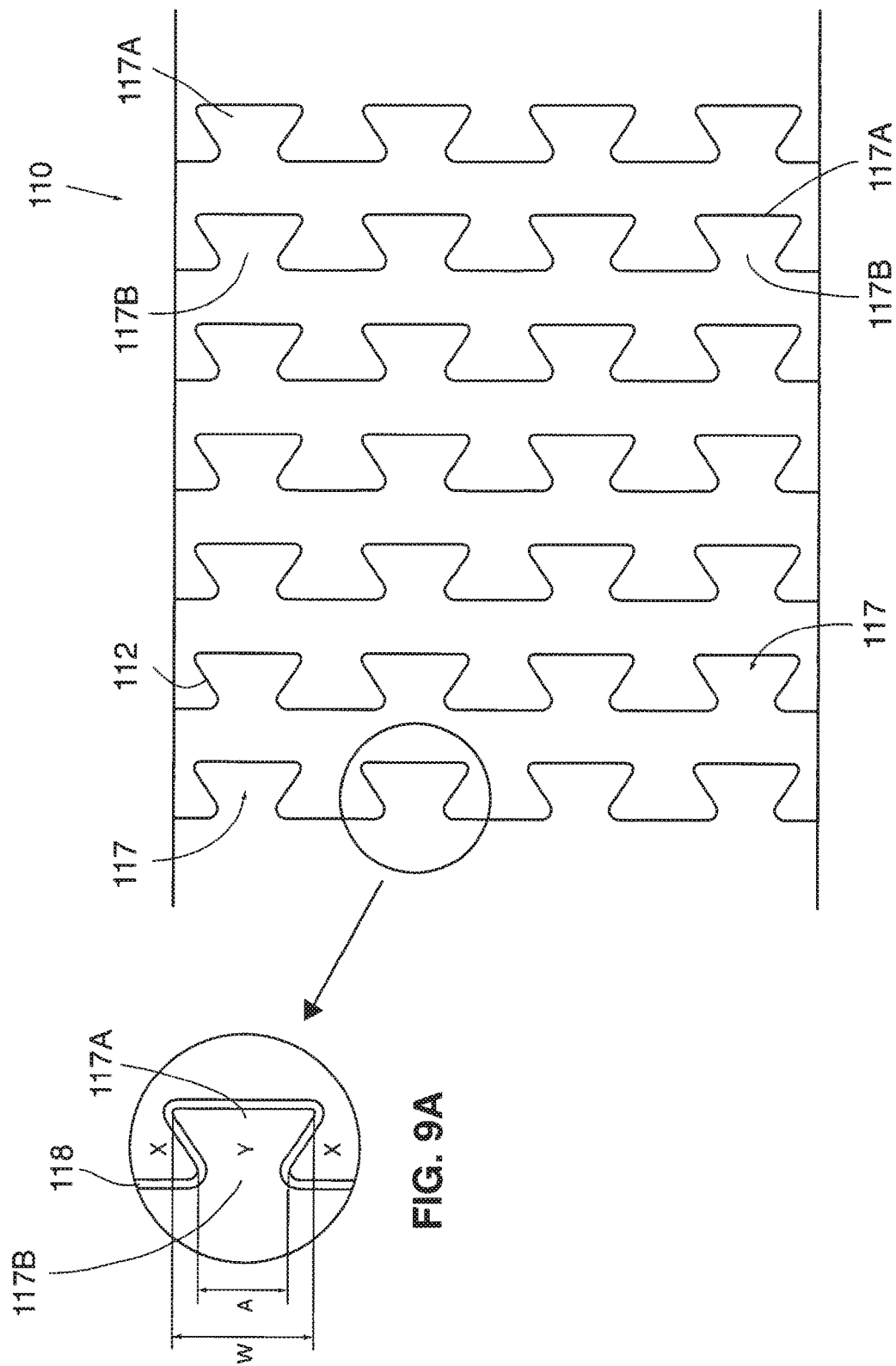

ABLATION CATHETER WITH FLEXIBLE ELECTRODE

CROSS REFERENCE TO RELATED APPLICATIONS

This patent application is a Continuation of U.S. patent application Ser. No. 15/348,823 filed Nov. 10, 2016, issued as U.S. Pat. No. 10,188,459, which is a Continuation of U.S. patent application Ser. No. 14/313,837 filed Jun. 24, 2014, issued as U.S. Pat. No. 9,510,903, which is a Continuation of U.S. patent application Ser. No. 13/910,771 filed Jun. 5, 2013, issued as U.S. Pat. No. 8,790,341, which is a Continuation of U.S. patent application Ser. No. 13/481,848 filed May 27, 2012, issued as U.S. Pat. No. 8,480,669, which is a Continuation of U.S. patent application Ser. No. 11/853,759 filed Sep. 11, 2007, issued as U.S. Pat. No. 8,187,267, which claims the benefit of U.S. Provisional Application No. 60/939,799 filed May 23, 2007. The '459 patent, the '903 patent, the '341 patent, the '669 patent, the '267 patent, and the '799 application are hereby incorporated by reference as though fully set forth herein.

BACKGROUND OF THE INVENTION

(1) Field of the Invention

The field of the invention is catheters, specifically ablation catheters.

(2) Background of the Invention

Ablation catheters with electrodes are generally known in the surgical art, and ablation electrode catheters with irrigation capabilities are also generally known in the art. Electrode catheters can be used for electrically mapping a body part, or to deliver therapy to a body part or both.

Using ablation electrodes to create lesions in heart tissues is known for treating heart conditions such as arrhythmia. Linear lesions are known to have some advantages over mere single point lesions. A single point lesion, as its name implies, is created by applying energy at a single point region of tissue. On the other hand, applying energy across an elongated region in a tissue creates a linear lesion.

Creating a linear lesion with only a tip electrode, however, is relatively time-consuming, labor-intensive, and generally impractical. A surgeon may use a typical single point electrode catheter to create linear lesion, by carefully dragging the single point electrode tip across the tissue while applying energy to the tissue surface.

U.S. Pat. No. 5,487,385, discloses a flexible catheter having ring electrodes disposed along its flexible shaft for creating a linear lesion. A surgeon may lay such catheter shaft across a tissue area, and allow the consecutively-arranged ring electrodes to ablate the target tissue using RF energy. The ring electrodes, however, must apply sufficient energy in order to create lesion areas that are connected, thus forming a single linear lesion. Applying too much RF energy, however, can cause unwanted damage. This arrangement often results in a series of spaced-apart single point lesions.

U.S. Pat. No. 6,063,080 discloses a catheter having an elongated electrode. This electrode has micro-slotting or micro-apertures across its surface to improve flexibility of the electrode, thus allowing a surgeon to lay the elongated electrode across a tissue surface.

Despite some desirable properties, such a longitudinal type electrode has several disadvantages. For example, the electrode requires a spherical structure at its tip to prevent the electrode from penetrating tissue. Also, a longitudinal type electrode cannot effectively create a linear lesion when the electrode is laid across a tissue having ridges. Thus, there is a continuing need for new ways to create linear lesions.

All referenced patents, applications and literatures are hereby incorporated by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply. The invention may seek to satisfy one or more of the above-mentioned desire. Although the present invention may obviate one or more of the above-mentioned desires, it should be understood that some aspects of the invention might not necessarily obviate them.

BRIEF DESCRIPTION OF THE INVENTION

Among the many different possibilities contemplated, embodiments of flexible tip electrodes for ablation catheters are disclosed. The contemplated flexible tip electrodes may have a dome-shaped tip. A cylindrical wall of the electrodes may have many openings extending through the wall, and such contemplated openings can have various shapes, sizes and overall configurations. The contemplated electrodes may be coupled to an energy source for ablating tissues.

The contemplated openings perforate through the thickness of the cylindrical wall to improve flexibility of the electrode. In some embodiments, the openings in the wall provide sufficient gaps in the wall to allow shortening of a length of the electrode, when a force is applied to the electrode in the linear direction, from its distal tip towards its proximal end.

Among the many possible sizes, contemplated openings in the electrode walls may have a width of between and including 0.01 to 0.50 millimeters.

Contemplated electrodes may have flexibility in terms of flexing and bending along a longitudinal length of the electrode. An ability to flex allows the electrode to bend between and including 0.2 degrees to 70 degrees, for example, along the longitudinal axis from a substantially straight position of the electrode. More specifically, the ability to flex may allow the tip electrode to bend between and including 5 degrees to 45 degrees along the longitudinal axis from a substantially straight position of the electrode.

Contemplated openings in the electrodes may also create flexibility in terms of shortening and lengthening the electrodes along the longitudinal length of the electrodes. In one embodiment, the electrode may shorten between and including 0.1% to 10% of a resting length of the electrode. More specifically, the gaps in the electrode walls may allow shortening of the length between and including 0.5% to 5% of the length; even more specifically, the gaps in the walls may allow shortening of the length between and including 0.1% to 2% of the resting length; and even shortening of the resting length between and including 0.1% to 0.5%.

Further, it is contemplated that the electrodes may have flexibility in terms of flexing and deforming the overall shape of the electrodes. For example, the electrodes may be deformed such that a cross sectional shape of the electrode is changed. In one embodiment, the electrode may deform like a marshmallow. Other embodiments only allow flexing and shortening, and do not deform like a marshmallow when subjected to pressure.

Another aspect of the invention is directed to the pattern of the openings in the electrodes. Contemplated electrodes may have at least one opening forming a linear gap in the electrode wall. The pattern may optionally form the following types of gap configurations: a straight line, a zig-zag line, a line that outlines alternating interlocking blocks, an undulating line, and a wavy line.

In an exemplary embodiment, the contemplated patterns may outline a plurality of blocks in the wall disposed on both sides of a gap, and each block may have a head and a neck, with the head being wider than the neck. Optionally, a first head of the block, which has a neck situated on one side of the gap, is disposed between a second and third heads both of which have necks positioned on the other side of the gap, and wherein the second and third heads have a shortest distance A between the two heads, with the distance A being shorter than a width of the first head.

Contemplated pattern of openings can also be described by focusing on the structure defining the openings. For example, a contemplated electrode wall may be defined by a spiraling member. The member may spiral about a longitudinal axis of the electrode forming a series of loops, and the member may have a stem and a plurality of protruding blocks disposed on both sides of the stem with each block extending transversely toward an adjacent loop. Contemplated blocks may have various shapes including a shape of an upside down triangle and bulbous shapes.

One embodiment includes a first head of a block disposed between a second and third heads of two other blocks that are connected to an adjacent loop. In another embodiment, a distance B between the second and third heads of an adjacent loop is shorter than a width of the first head, thereby restricting relative movement of two adjacent loops away from each other. The member is contemplated to spiral about the longitudinal axis with a pitch between and including 0.5 to 10 degrees. Similarly, the general layout of contemplated patterns of openings in preferred embodiments is that the pattern spirals around the electrode with a pitch between and including 0.5 to 10 degrees. Optimally, a pitch of approximately four degrees is desired. A pitch of approximately two degrees is optimal. Generally, the higher the degree of pitch the stiffer the electrode becomes.

Contemplated electrodes may have gaps disposed between the first head and a stem of the adjacent loop, allowing freedom of movement of two adjacent loops relative to each other.

In some embodiments, a coil may be disposed within the lumen to provide structural integrity to the electrodes. In still further embodiments, the coil may resiliently keep the electrode in a pre-determined configuration. In one embodiment, the pre-determined configuration may be straight. In another embodiment, the pre-determined configuration may be an arcuate shape. The contemplated coil may resiliently bias the electrode to stretch in a linear direction parallel to the longitudinal axis of the electrode. It other words, the coil optionally biases the tip electrode to stretch lengthwise. Optionally, the coil, or the electrode, or both, can be comprised of shape memory metal.

In still further other embodiments, the catheter may include irrigation features, wherein a cooling fluid may be delivered in a lumen and pass through the gaps to the outside of the electrode.

Various features, aspects and advantages of the present invention will become more apparent from the following detailed description along with the accompanying drawings in which like numerals represent like components.

BRIEF DESCRIPTION OF THE DRAWINGS

FIG. 2 is a perspective view of another embodiment of a flexible tip electrode according to an aspect of the inventive subject matter.

FIGS. 2A-2D are alternative embodiments of the flexible tip electrode shown in FIG. 2.

FIGS. 7A-7C are illustrative views of some of the contemplated embodiments of the invention in operation.

FIG. 9 is a side view of an embodiment of flexible tip electrode with interlocking block pattern.

FIG. 9A is a close-up view of a block from the interlocking block pattern of FIG. 9.

DETAILED DESCRIPTION OF THE INVENTION

The invention and its various embodiments can now be better understood by turning to the following detailed description of numerous embodiments, which are presented as illustrative examples of the invention defined in the claims. It is expressly understood that the invention as defined by the claims may be broader than the illustrated embodiments described below.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed herein even when not initially claimed in such combinations.

As used herein, the terms "spiral," or "spiraling" in conjunction with electrode wall and its patterns, refers to a circling configuration where a series of loops are formed. The loops have substantially the same diameter, and resemble that of a coil. These terms do not refer to circling on a same plane with increasing circumference.

As used herein, the terms "gap," or "opening" in conjunction with a cutting pattern in the electrode wall, refers to a perforation that is more than a mere groove (which is only a surface cut that does not cut through the thickness of the wall). Gaps and openings are perforated through the thickness of the electrode wall.

Embodiments of ablation catheters having a flexible tip electrode for creating linear lesions in tissues are disclosed. The flexibility of the tip electrodes increases an electrode-to-tissue surface area, and in turn improves ablation of tissue. Especially in tissue where ridges are present, the flexible tip electrodes can be dragged across the ridges with improved continuous electrode-to-tissue contact.

Among the many different possibilities contemplated, the flexible tip electrode for an ablation catheter is generally a hollow cylindrical structure with a lumen. The tip electrode has a round dome-shaped terminal end. The cylindrical wall of the electrode may have many openings, and such openings can have various shapes, sizes and overall configurations.

Figure 1A:
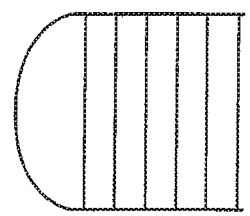
FIGS. 1A-1C are alternative embodiments of the flexible tip electrode shown in FIG. 1
Figure 1B:
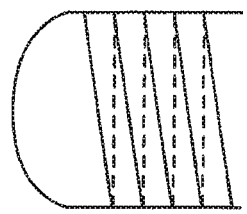
Figure 1:
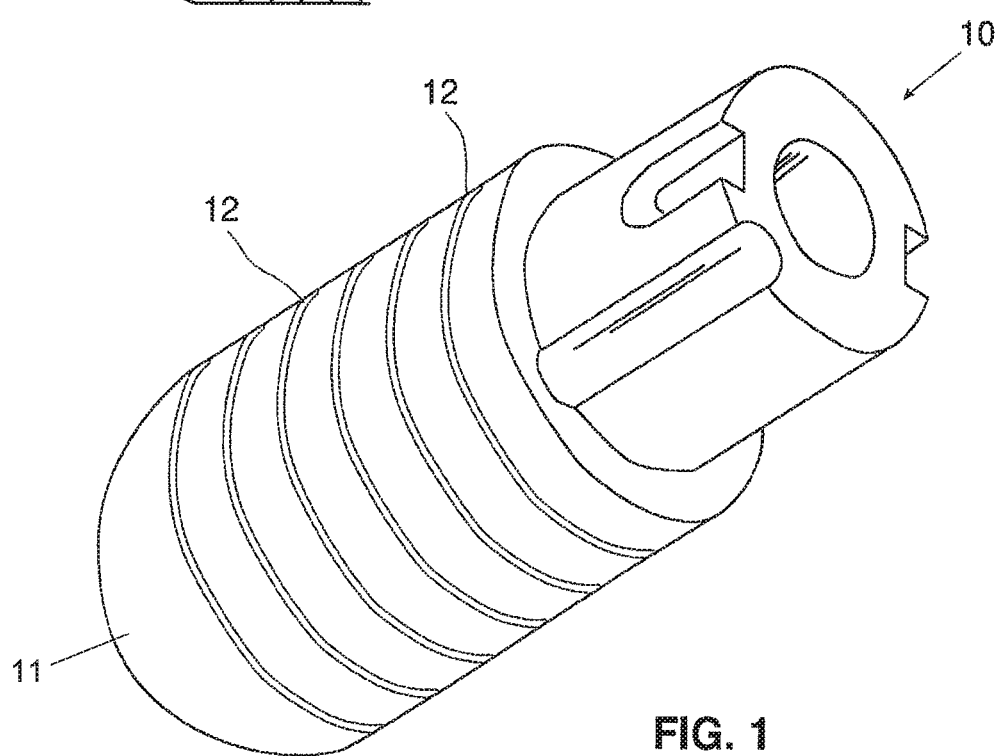
FIG. 1 is a perspective view of an embodiment of a flexible tip electrode according to an aspect of the inventive subject matter.
Figure 1C:
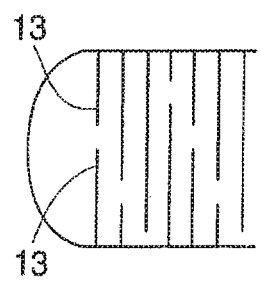

Referring now to FIG. 1, an exemplary tip electrode 10 has a dome tip 11, and has a 15 series of ring-like grooves 12 disposed about the tip electrode, spaced equidistant from each other along a longitudinal length of the tip electrode. Each ring-like groove 12 may form a continuous loop (as it is shown in FIG. 1A). Alternatively, all or part of the series of rings can be in a spiral configuration (as shown in FIG. 1B) around the outside surface of the tip electrode. In another embodiment, the electrode may include some rings that do not form a continuous loop, but leaves the two terminal ends (13) of the groove (as shown in FIG. 1C) apart. A further embodiment may include a combination of these configurations.

As used herein, the term "groove," refers to a surface channel, and does not perforate through the wall of the electrode. In other embodiments, the grooves are replaced by cutting patterns that are thoroughly perforated through the thickness of the wall of the electrode. In the embodiment shown in FIG. 1A, however, if each complete loop is thoroughly cut through, some type of additional supporting structure is required to connect the severed pieces together. For example, an inner coil may be provided within the lumen (see FIGS. 14A and 14B).

Referring now to FIG. 2, the grooves 12 are more spaced apart than that shown in FIG. 1. Here, each ring-like groove does not form a continuous loop, and terminal ends 13 of each groove slightly offset each other to maintain some degree of desired rigidity in the electrode. Note that in FIGS. 2A through 2B, the terminal ends 13 of the groove do not overlap. FIG. 2C illustrates another embodiment where the terminal ends 13 do overlap, although they do not meet to form a continuous loop. Another contemplated embodiment may include a combination of grooves with overlapping and grooves with non-overlapping terminal ends. As is true with all embodiments disclosed in the instant application, grooves 12 may be replaced with cutting patterns that are thoroughly perforated through the thickness of the electrode wall.

FIG. 2D illustrates another embodiment where the ring-like grooves 12 are half loops extending across about 180 degrees of the electrode's cylindrical surface. Many other positions of half loops are also contemplated. In other embodiments, some or all grooves may extend across more or less than 180 degrees of the electrode's cylindrical circumference.

Figure 3A:
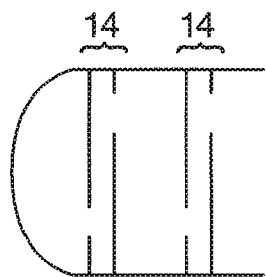
FIG. 3A is a side view of the embodiment shown in FIG. 3.
Figure 3:
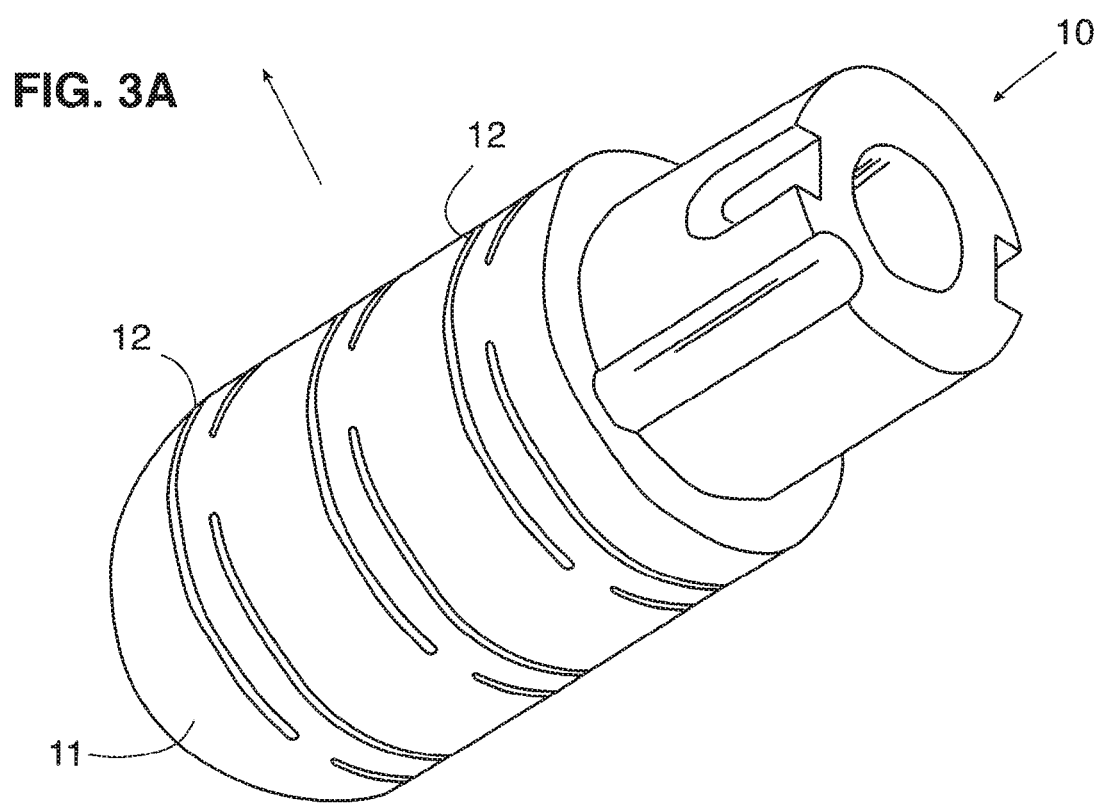
FIG. 3 is a perspective view of another embodiment of a flexible tip electrode according to an aspect of the inventive subject matter.

In FIG. 3, three set of grooves 12 are provided, each set 14 having two non-continuous loops. As shown in FIG. 3A, the two grooves 12 in a single set 14 do not form a spiral. Spacing between the sets 14 is generally greater than spacing between the two loops in the same set.

Figure 4A:
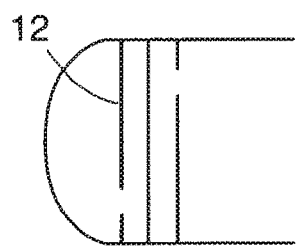
FIGS. 4A-4B are alternative embodiments of the flexible tip electrode shown in FIG. 4.
Figure 4B:
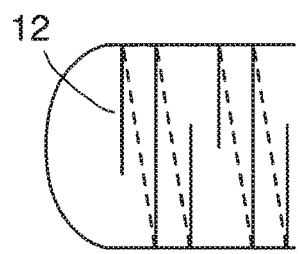
Figure 4:
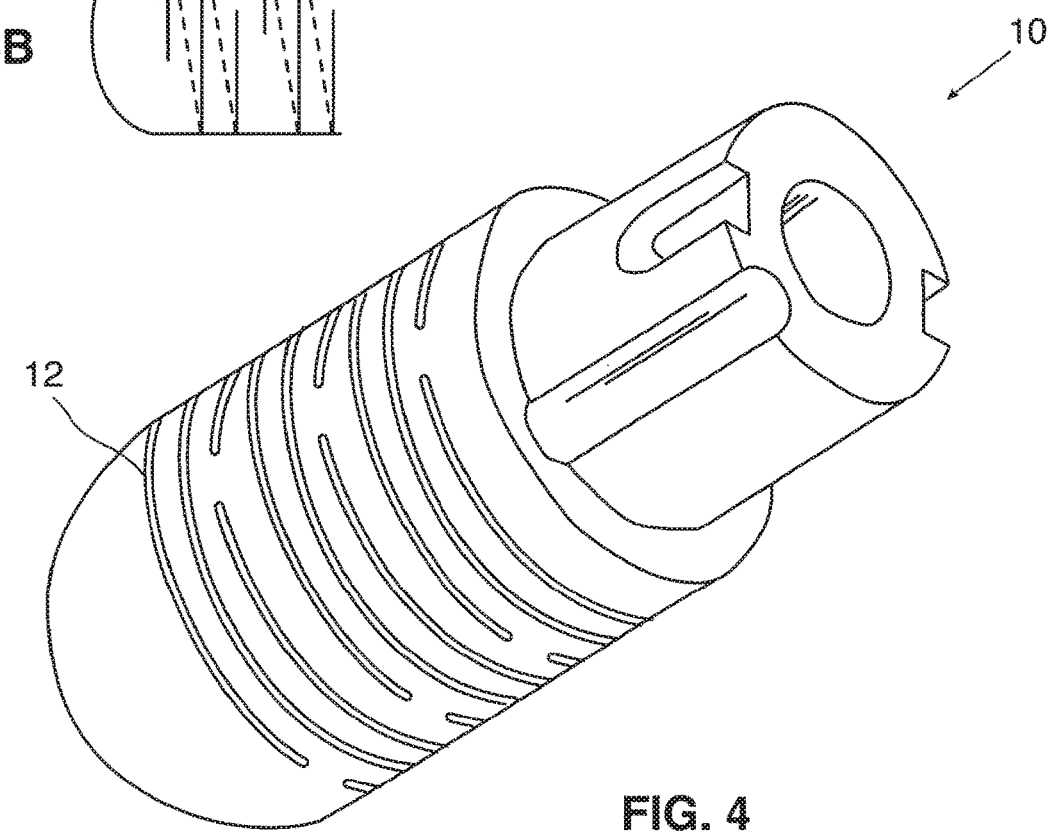
FIG. 4 is a perspective view of another embodiment of a flexible tip electrode 20 according to an aspect of the inventive subject matter.

In FIG. 4, another embodiment provides sections of ring-like grooves 12. In the embodiment shown in FIG. 4A, the rings are non-continuous loops that do not connect with each other. In the embodiment shown in FIG. 4B, each section is a spiral groove 12 collectively forming a continuous spiral groove.

Figure 5:
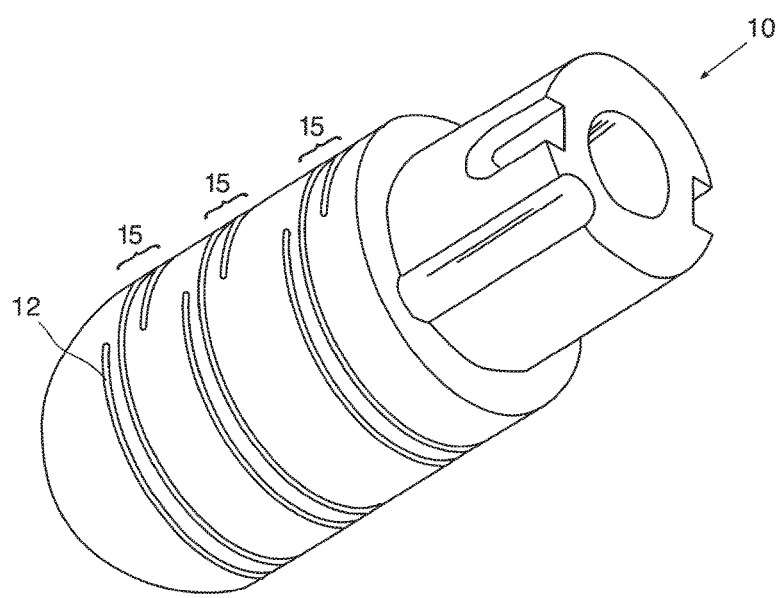
FIG. 5 is a perspective view of another embodiment of a flexible tip electrode according to an aspect of the inventive subject matter.

FIG. 5, illustrates another embodiment with three sets of rings. Each set 15 is shown to be a continuous spiral groove.

Figure 6:
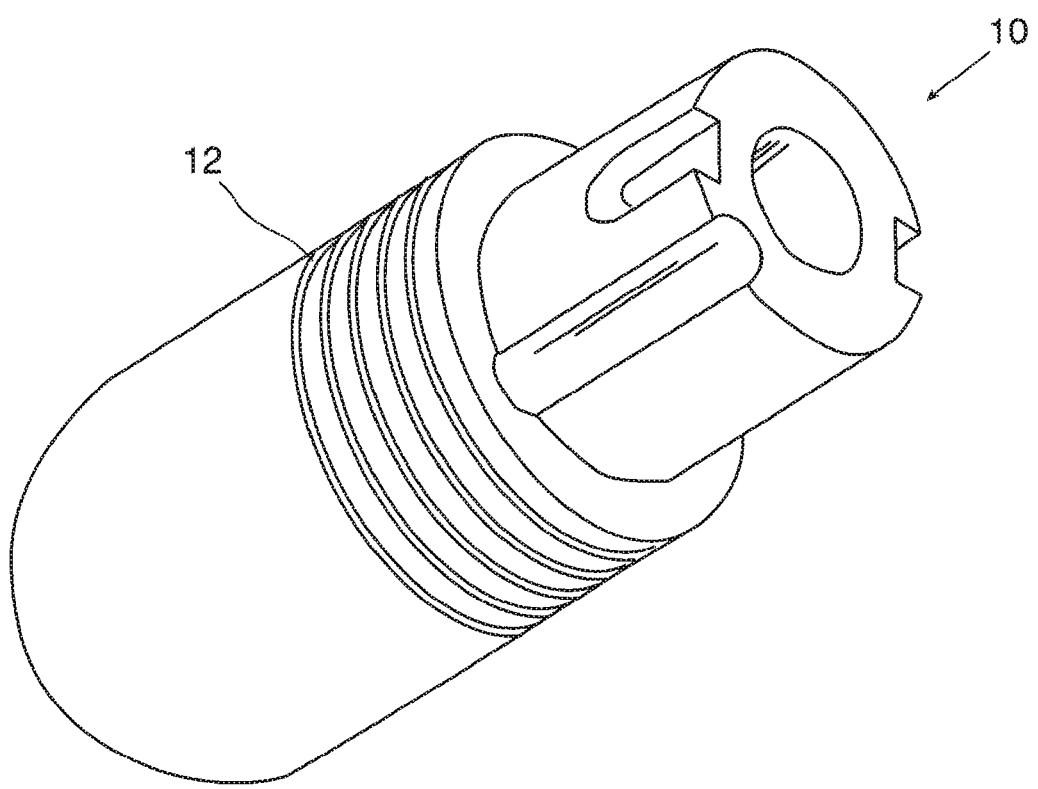
FIG. 6 is a perspective view of another embodiment of a flexible tip electrode according to an aspect of the inventive subject matter.

FIG. 6 illustrates another contemplated embodiment where a series of ring-like grooves 12 are disposed equidistant from each other along a proximal section of the tip electrode 10. Each ring may or may not form a continuous loop. Another embodiment provides that all or at least some of the groves each create a continuous loop. Embodiments applicable to this Figure provide a desired rigidity in the distal portion of the tip electrode 10.

FIGS. 7A through 7C illustrate embodiments of the invention in use. One aspect of the invention allows and facilitates dragging of the flexible tip electrode 10 across a tissue surface. Here, the flexible electrode 10 deforms and/or flexes when it is dragged across a tissue surface. The flexible and deformable properties of these embodiments create greater electrode-to-tissue surface area. In FIG. 7A, the tip electrode has a cut pattern 12 that includes relatively straight lines that are thoroughly perforated through the thickness of the electrode. In FIG. 7B, a tip electrode with zig-zag design cutting pattern allows even greater flexibility that that of FIG. 7A. In FIG. 7C, however, the catheter tip electrode has grooves at the neck region where the electrode is attached to a catheter, allowing some degree of flexibility in a more rigid tip electrode.

Figure 8A:
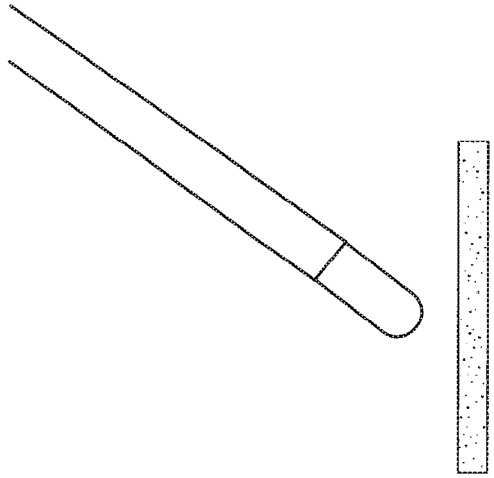
FIGS. 8A-8C are illustrative views of some of the contemplated embodiments of the invention in operation.
Figure 8B:
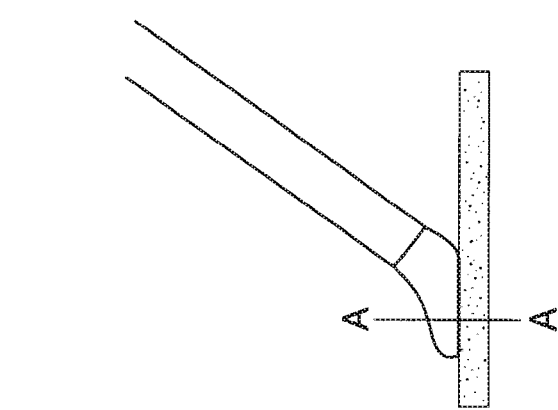
Figure 8C:
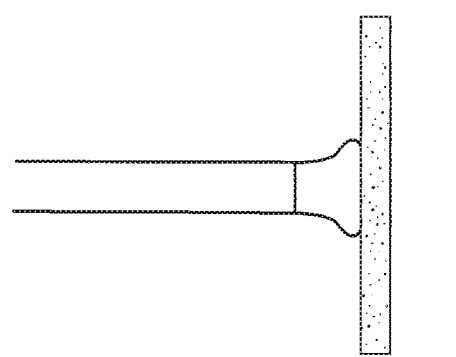
Figure 8D:
FIG. 8D is a cross-sectional view of line A-A in FIG. 8B.
Figure 8E:
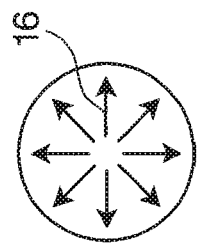
FIG. 8E illustrates electrode-to-surface area in FIG. 8C.

FIGS. 8A through 8E illustrate how some embodiments of the current invention may advantageously deform in other ways to create greater electrode-to-tissue surface area. In FIG. 8A, an embodiment of the electrode is ready to make contact with tissue surface. The electrode makes contact with tissue surface (FIG. 8B) and the tip electrode deforms. A cross sectional area along line A-A becomes oval in shape (FIG. 8D). This embodiment not only flexes along a longitudinal axis, but also expands laterally. When the angle between the tissue surface and a longitudinal axis of the catheter body gets closer to a 90 degree angle (FIG. 8C), the flexible tip deforms and shortens due to downward pressure against the tissue surface. FIG. 8E shows a cross section of the tip electrode in FIG. 8C. The electrode-to-tissue surface area (represented by the circle in FIG. 8E) further expands outwardly (represented by arrows 16), as the catheter is pressed further towards the tissue surface. One contemplated embodiment that has the capability as shown in FIGS. 8A through 8E is the tip electrode with a zip-zag cut pattern as shown in FIG. 7B.

Referring now to FIG. 9, an exemplary embodiment of flexible tip electrode 110 has a cutting pattern that outlines alternating interlocking blocks 117. In the illustrated embodiment, the contemplated blocks 117 are disposed on both sides of the gap 118 created by the cutting pattern. Each block has a head 117A and a neck 117B, and the head is wider than the neck. In this interlocking pattern, A first head (represented by "Y" in FIG. 9A) of the block 117, which has a neck 117B situated on one side of the gap 118, is disposed between a second and third heads (represented by "X" in FIG. 9A), both of which have necks situated on the other side of the gap 118. These blocks X and Y are interlocked because the wider head portion of one head is locked between the narrower neck portions of the two adjacent blocks 117. For example, the second and third heads X in FIG. 9A has a shortest distance A (shown as "A" in FIG. 9A) between the two heads, and distance A is shorter than a width (shown as "W" in FIG. 9A) of the first head Y.

Figure 10:
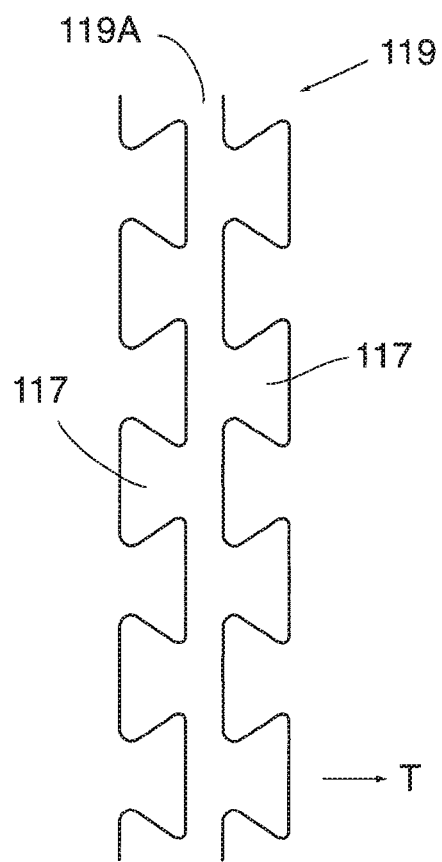
FIG. 10 is a view of a section of the electrode wall that makes up a stem with interlocking blocks.
Figure 11:
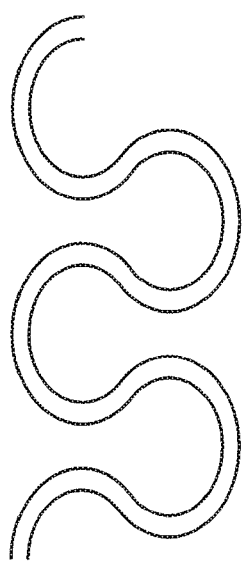
FIG. 11 is a view of an alternative design of bulbous interlocking blocks.

Contemplated patterns of openings can also be described by focusing on the structures of the electrode wall, instead of focusing on the shape of the gap 118. For example, in FIG. 10, a contemplated electrode wall is comprised of a spiraling member 119. The member 119 spirals about a longitudinal axis of the electrode forming a series of loops (see FIG. 9), and wherein the member 119 has a stem 119A and a plurality of protruding blocks 117 disposed on both sides of the member 119. Each block 117 transversely extends (see arrow T in FIG. 10) toward an adjacent loop in the electrode wall. Contemplated blocks can have various shapes. For example, at least some of the blocks may have a shape of an upside down triangle, where one angle of the triangle represents the neck region. Alternatively, blocks with bulbous shape such as ones shown in FIG. 11 may be utilized. Contemplated heads of the bulbous shapes are wider than their corresponding necks.

Referring back to FIG. 9A, this embodiment includes a first head (Y) of a block 117 disposed between a second and third heads (X) of two other blocks 117 that are connected to an adjacent loop. Further, a distance (A) between the second and third heads (X) of an adjacent loop is shorter than a width (W) of the first head (Y), thereby restricting relative movement of two adjacent loops away from each other.

The member 119, having an axis 119B, may spiral about the longitudinal axis ("F" of FIG. 12) with a pitch ("P" of FIG. 12) between and including 0.5 to 10 degrees. To describe it in another way, the patterns of gaps 118 spirals around the longitudinal axis ("F") with a pitch between and including 0.5 to 10 degrees.

The contemplated openings perforate through the thickness of the cylindrical wall to improve flexibility of the electrode. The flexibility refers to flexing and bending along the longitudinal length of the electrode. For example, the ability to flex allows an approximately 4 mm length of the electrode to bend in an angle G (see FIG. 12B) that falls between and including 0.2 degrees to 70 degrees relative to the longitudinal axis from a substantially straight position. More specifically, the ability to flex allows the approximately 4 mm length to bend between and including 5 degrees to 50 degrees relative to the longitudinal axis from its substantially straight position. Even more specifically, the ability to flex allows the approximately 4 mm length to bend about 45 degrees relative to the longitudinal axis from its substantially straight position.

Figure 12A:
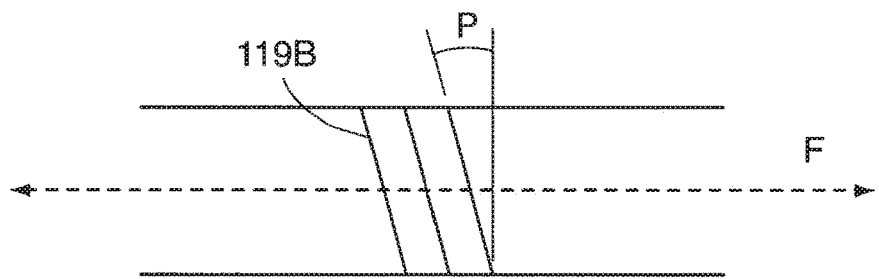
FIG. 12A is an illustrative view of the degree of pitch of the spiraling member.
Figure 12B:
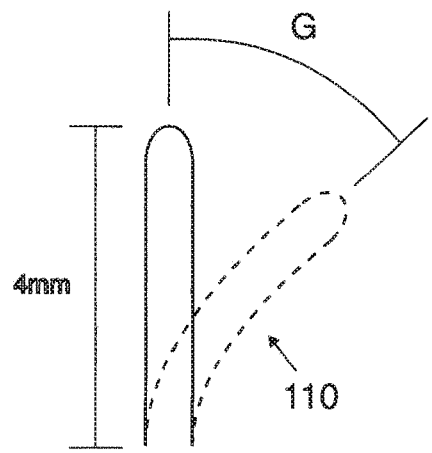
FIG. 12B is an illustrative view of the degree of flexing for the flexible tip electrode.
Figure 12C:
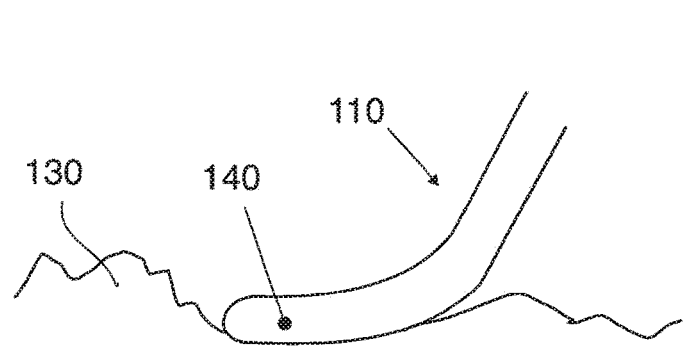
FIG. 12C is an illustrative view of an embodiment of the tip electrode being dragged across tissue with ridges.
Figure 12D:
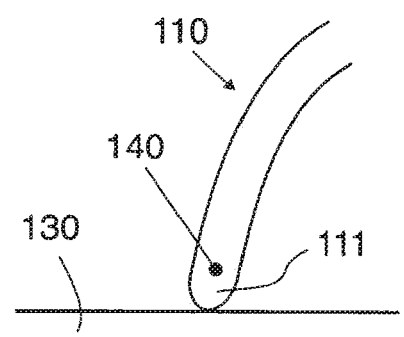
FIG. 12D is an illustrative view of an embodiment of the tip electrode being dragged across smooth tissue surface.

FIGS. 12C and 12D illustrate an electrode 110 being dragged across tissue 130. In FIG. 12C, the electrode 110 is flexed and pressed against tissue 130, which has a relatively irregular surface. Being able to flex provides better contact with the target tissue, for example, in the trabeculated endocardial tissue where there are valleys, ridges, and pockets. Here, electrode-to-tissue contact area is increased by using the side of the electrode 110 to deliver energy for ablation. The increased contact surface increases the likelihood of creating larger lesions at a given contact force and power setting. This enables deeper ablation without having to increase the power setting, as higher power setting undesirably increases the likelihood of coagulation. In FIG. 12D, the dome tip 111 is used to delivery energy to tissue 130. Flexible electrode 110 absorbs any contraction or vibration of tissue 130, and improves continuous tissue contact in a beating heart during systole and diastole, whether the electrode contacts the tissue 130 in parallel, perpendicular, or every angle in-between orientation, or whether the electrode is stationary at one location or when the electrode is in motion being dragged. Without such flexibility, a standard rigid tip electrode would "jump off" of the tissue in response to a beating heart.

Optionally, flexible electrode may have force-sensing capability to measure contact force in different directions. For example, a strain gage, a fiber optic sensor, or other sensors 140 may be disposed within the electrode to measure amount of force causing the electrode to flex, and to shorten. Such data can be collected and transmitted to the physician to monitor ablation progress. This may prevent accidental piercing of the target tissue when too much perpendicular force is applied to press the dome 111 into the tissue.

Unlike known elongated electrodes (e.g., U.S. Pat. No. 6,063,080), which can be laid across a tissue to create relatively longer linear lesions, the current inventive subject matter has the unexpected advantage of improving precision in mapping and control at specific locations within the heart for more precise ablation, especially in relatively tight anatomical structures. Known elongated electrodes have difficulty positioning in such tight anatomical structures.

One unexpected advantage in having a flexible tip electrode is minimized "flipping." When a standard rigid tip electrode is manipulated within a cavity having valleys and pockets, the tip electrode can get caught in the pocket when the physician continues to apply force in an attempt to move the tip electrode. In such instance, a standard rigid tip electrode would remain caught in the pocket until sufficient force is built, and the tip electrode suddenly "flip" out of the pocket. Such "flipping" is highly undesirable and should be avoided. The instant invention with a flexible tip greatly minimizes "flipping," and allows smoother dragging across valleys and pockets.

Figure 13:
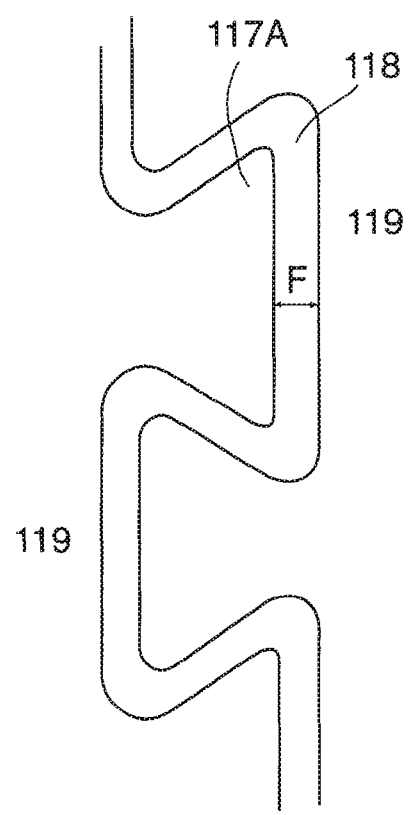
FIG. 13 is a close-up view of one embodiment of the gap in the electrode wall.

Referring now to FIG. 13, the openings in the wall provide a sufficient gap 118 in the wall to allow shortening of a length of the electrode, when a force is applied to the electrode in the linear direction. The gap 118 disposed between a head 117A and a stem 119 of the adjacent loop, allows a freedom of movement ("F") along the longitudinal axis between two adjacent loops relative to each other. Likewise, the gap 118 between adjacent heads 117A provides a freedom of movement for lengthening of the electrode along the longitudinal length of the electrode.

In one embodiment, the electrode can shorten between and including 0.2% to 10% of a resting length of the electrode. In one embodiment, the gap in the wall allows shortening of the length between and including 0.1% to 8% of the length. More specifically, the gap in the wall allows shortening of the length between and including 0.5% to 5% of the length, and even more specifically, the gap in the wall allows shortening of the length between and including 0.1% to 0.5% of the length.

Figure 13A:
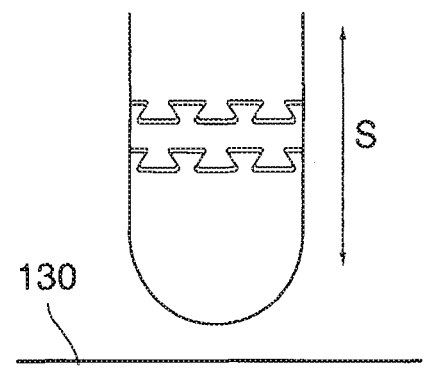
FIG. 13A is a side view of the electrode in FIG. 13 at rest.
Figure 13B:
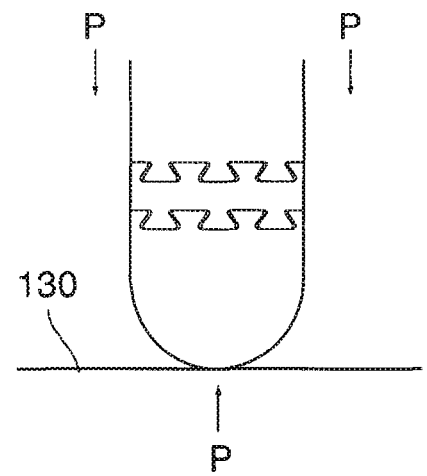
FIG. 13B is a side view of the electrode in FIG. 13 when pressed against a tissue surface.

In FIG. 13A, the electrode at rest has a freedom of movement ("F") shown, because the electrode at rest assumes a pre-determined shape stretching in the "S" direction. When the electrode is applied to a tissue 130, pressing force (arrows "P" in FIG. 13B) causes the electrode to shorten, against the stretching force "S." Once shortened, the width of the gap illustrating freedom of movement ("F") is minimized (see FIG. 13B).

Figure 14A:
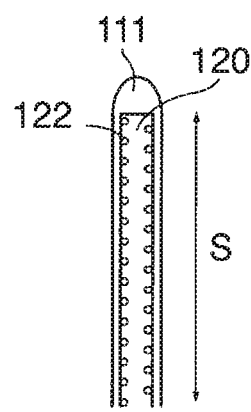
FIG. 14A is a longitudinal cross-sectional view of one embodiment of the tip electrode having a coil at rest.
Figure 14B:
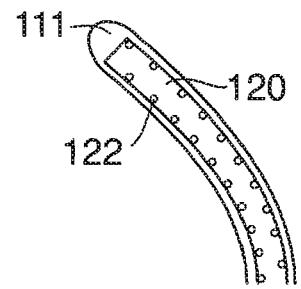
FIG. 14B is a longitudinal cross-sectional view of another embodiment of the tip electrode having a coil with an arcuate shape at rest.

The stretching force "S" may be provided by a shape memory alloy in the electrode 15 wall. Alternatively, FIG. 14A shows a cross sectional view of an electrode where the stretching force "S" is provided by a coil 122 in the lumen 120. The coil 122 provides structural integrity to the electrode and resiliently keeps the electrode in a pre-determined configuration at rest. In one embodiment, the pre-determined configuration is straight. In another embodiment, the pre-determined configuration at rest is an arcuate shape (see FIG. 14B). The contemplated coil resiliently biases the electrode to stretch in an endwise direction ("S" in FIG. 14A) parallel to the longitudinal axis of the electrode. It other words, the coil optionally biases the tip electrode to stretch lengthwise.

The coil, or the electrode, or both, can include a shape memory metal. The flexible tip electrode can be made of suitable conductive and biocompatible materials, suitable for ablation temperature; such materials include natural and synthetic polymers, various metals and metal alloys, Nitinol, naturally occurring materials, textile fibers, and all reasonable combinations thereof. In one embodiment, the tip electrode includes MP3SN alloy.

The catheter can optionally couple to an irrigation system, wherein a cooling fluid is 30 delivered in the lumen and allowed to pass through the gap to outside of the electrode. An internal irrigation system is also possible. Also, the catheter can optionally couple to an energy source, such as a radio frequency (RF) generator to provide energy needed for tissue ablation. An example of such RF generator is one disclosed in U.S. Pat. No. 6,235,022.

Figure 15A:
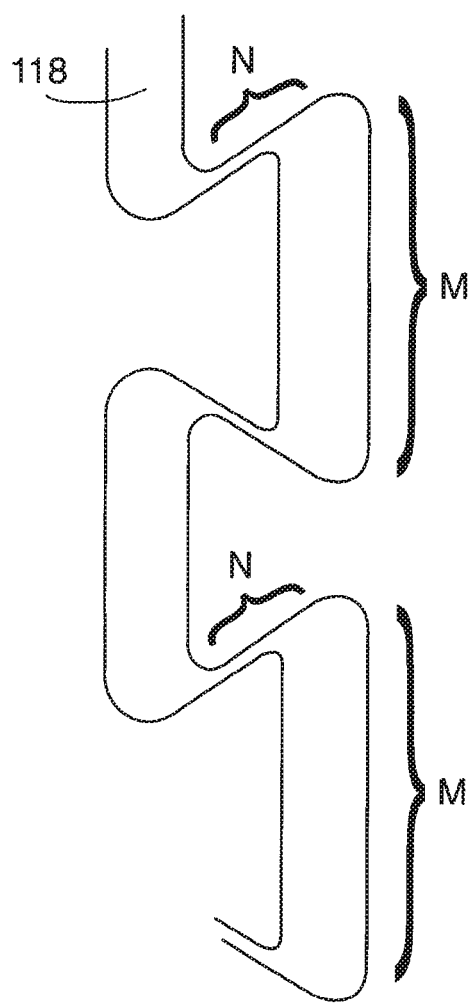
FIG. 15A is an illustrative view showing the shape and width of the gap as is cut by laser.

Contemplated inventive subject matter also includes methods of making a flexible electrode for an ablation catheter by providing a hollow cylindrical electrode, and applying a laser to the cylindrical electrode to cut through a wall of the electrode. The laser cuts the wall in a pre-determined pattern that may continuously spiral around the cylindrical electrode. As shown in FIG. 15, the cut creates a gap 118 that may be consistently wider in some sections (M) and narrower in some other sections (N). The wider sections (M) are substantially parallel to a longitudinal axis (119B in FIG. 12) of a spiral loop. The narrower sections (N) may connect wider sections (M) together, and may be disposed generally transverse the longitudinal axis (119B) of the spiral loop.

The wider sections allow freedom of movement between adjacent spiral loops, making it possible to shorten the electrode when a force is applied at a distal end of the electrode towards a proximal end.

Figure 15B:
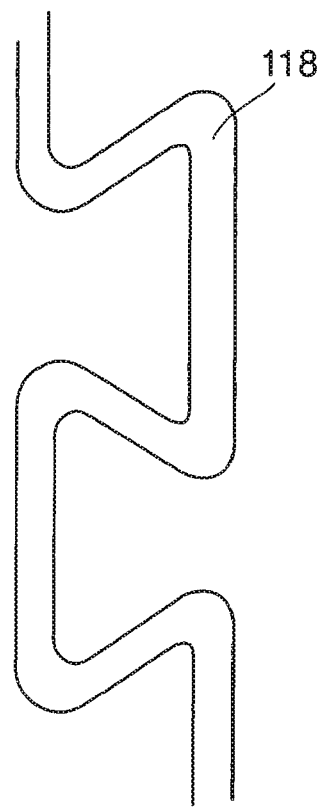
FIG. 15B is an illustrative view of showing a consistent width of the gap as is cut by laser.
Figure 16:
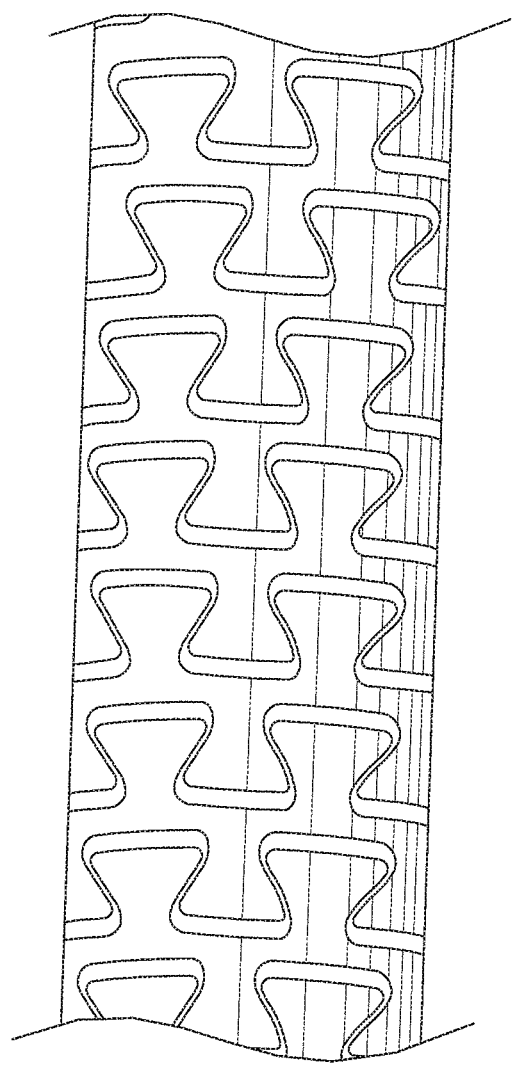
FIG. 16 is a photograph of an embodiment of the present invention, illustrating size and dimension of interlocking blocks in relative to the width of the catheter tip. The entire width of the catheter tip is shown.
Figure 17:
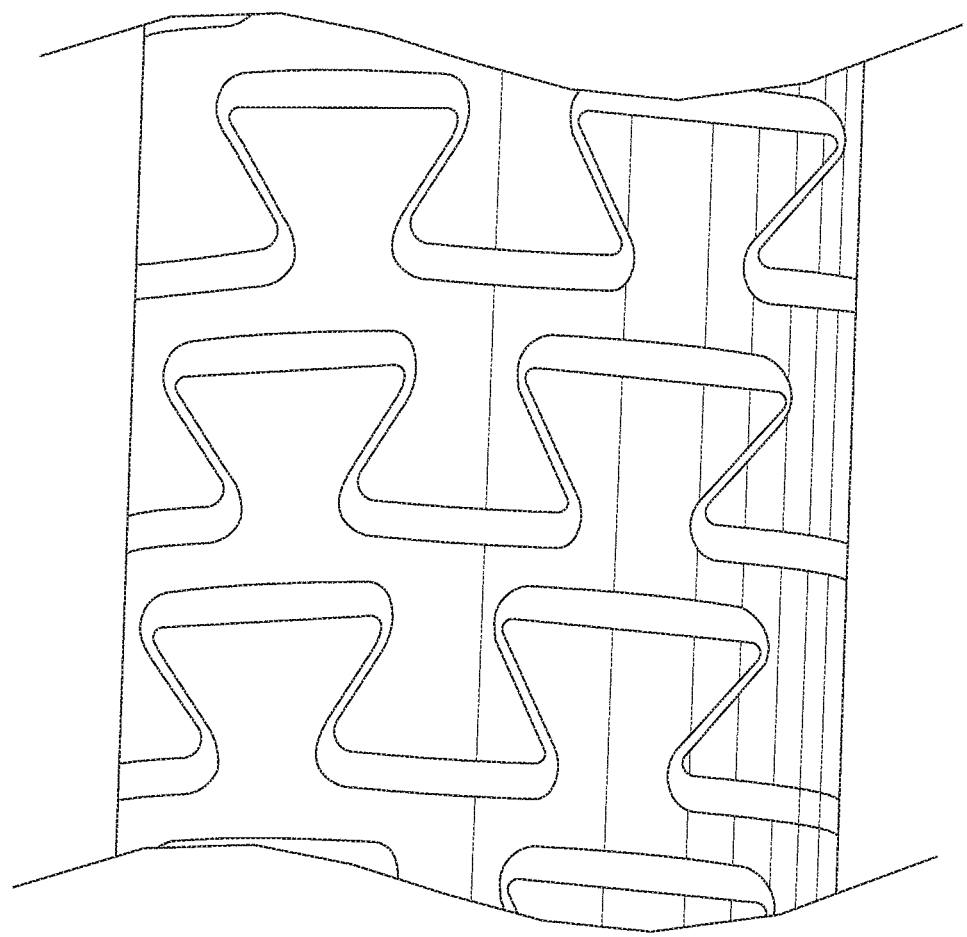
FIG. 17 is a close-up photograph of an embodiment of the interlocking blocks. The entire with of the catheter tip is not shown here.

FIG. 15B illustrates another embodiment where the laser also cuts the wall in a pre-determined pattern, where the gap 118 created by the laser has generally consistent width. A coil is subsequently installed in the lumen of this electrode to provide stretching force to create wider sections and narrower sections as illustrates in FIG. 15A.

Coatings such as gold and platinum can be applied to the electrode to increase thermo-conductivity. The electrode can also be coated with heparin to provide anticoagulation effect. In addition, the electrode may be electro-polished to reduce sharp edges.

The inventive subject matter also includes methods of performing linear ablation using an embodiment of the present invention. As with typical ablation catheters, a physician can perform mapping using the electrodes, and determine a target site for ablation. Once determined, the physician drags the flexible tip electrode across the target tissue to start ablation while applying energy to the tissue. Because the electrode is flexible, the electrode can be more easily dragged across tissue surfaces having ridges and bumps while keeping constant electrode-to-tissue contact. And because the gaps in the electrode wall allows the electrode to be shortened when pressed tip-down against tissue surface, the chances of accidental tissue-piercing is lessened.

Thus, specific embodiments and applications of flexible tip electrode have been disclosed. It should be apparent, however, to those skilled in the art that many more modifications besides those already described are possible without departing from the inventive concepts herein. The inventive subject matter, therefore, is not to be restricted except in the spirit of the appended claims.

The invention claimed is:

1. An ablation catheter comprising a catheter body and an electrode disposed at a distal end of the catheter body, the electrode comprising an axial dimension extending along an axis and a sidewall provided with one or more openings extending therethrough, the sidewall comprising a flexibility that allows shortening of the electrode axial dimension when a force is applied to the electrode along the axis.

2. The catheter as recited in claim 1, wherein the electrode further comprises a force-sensing member configured to provide information about the amount and direction of contact force exerted on tissue by the electrode.

3. The catheter as recited in claim 1, wherein the catheter further comprises a force-sensing capability configured to determine contact force in different directions.

4. The catheter as recited in claim 1, wherein the catheter further comprises a fluid delivery lumen in fluid communication with the one or more openings.

5. The catheter as recited in claim 1, wherein the electrode is configured to deform and flex when it is dragged across a tissue surface.

6. The catheter as recited in claim 1, wherein the electrode comprises a flexibility that enables it to radially deform such that a cross sectional shape of the electrode is changed.

7. The catheter as recited in claim 1, wherein the electrode comprises a flexibility that enables the sidewall to adopt different operating configurations relative to the axis.

8. The catheter as recited in claim 7, wherein the different operating configurations include at least one of a resting length configuration, a substantially straight configuration, and configurations having changed cross sectional shapes.

9. The catheter as recited in claim 1, wherein the sidewall is configured such that the one or more openings enable bending movement of the electrode relative to the axis of the electrode when the electrode impinges upon a tissue surface, and configured for directed fluid egress from a portion of the openings toward the tissue surface.

10. The catheter as recited in claim 1, wherein the openings provide an axial freedom of movement and are configured to allow the electrode to bend between about 5 degrees 50 degrees relative to the axis of the electrode from its substantially straight position when the electrode impinges upon a tissue surface.

11. The catheter as recited in claim 1, wherein the electrode is configured to deform when contact is made with a tissue surface parallel to the axis such that the electrode-to-tissue surface area increases and the electrode deforms laterally as the catheter is pressed further towards the tissue surface.

12. The catheter as recited in claim 11, wherein the electrode deforms like a marshmallow upon contact with the tissue surface.

13. An ablation catheter comprising a catheter body and an electrode disposed at a distal end of the catheter body, the electrode comprising an axial length along a longitudinal axis and a sidewall provided with one or more openings extending therethrough, wherein the electrode is configured to deform when contact is made with a tissue surface parallel to the longitudinal axis such that the electrode-to-tissue surface area increases and the electrode deforms laterally as the catheter is pressed further towards the tissue surface.

14. The catheter as recited in claim 13, wherein the electrode further comprises a force-sensing member configured to provide information about the amount and direction of contact force exerted on tissue by the electrode.

15. The catheter as recited in claim 13, wherein the catheter further comprises a force-sensing capability configured to determine contact force in different directions.

16. The catheter as recited in claim 13, wherein the electrode is configured to deform and flex when it is dragged across a tissue surface.

17. The catheter as recited in claim 13, wherein the electrode comprises a flexibility that enables the sidewall to adopt different operating configurations relative to the longitudinal axis, wherein the different operating configurations include configurations having changed cross sectional shapes.

18. The catheter as recited in claim 13, wherein the electrode deforms like a marshmallow upon contact with the tissue surface.

19. An ablation catheter comprising a catheter body and an electrode disposed at a distal end of the catheter body, the electrode comprising an axial length along a longitudinal axis and a sidewall provided with one or more openings extending therethrough, wherein the electrode comprises a flexibility that enables it to radially deform such that a cross sectional shape of the electrode is changed.

20. The catheter as recited in claim 19, wherein the electrode is configured to deform when contact is made with a tissue surface parallel to the longitudinal axis such that the electrode-to-tissue surface area increases and the electrode deforms laterally as the catheter is pressed further towards the tissue surface.

21. The catheter as recited in claim 19, wherein the electrode further comprises a force-sensing member configured to provide information about the amount and direction of contact force exerted on tissue by the electrode.

22. The catheter as recited in claim 19, wherein the catheter further comprises a force-sensing capability configured to determine contact force in different directions.

23. The catheter as recited in claim 19, wherein the electrode is configured to deform and flex when it is dragged across a tissue surface.

24. The catheter as recited in claim 19, wherein the openings provide an axial freedom of movement and are configured to allow the electrode to bend between about 5 degrees 50 degrees relative to the longitudinal axis of the electrode from its substantially straight position when the electrode impinges upon a tissue surface.

25. The catheter as recited in claim 19, wherein the sidewall is configured such that the one or more openings enable bending movement of the electrode relative to the longitudinal axis of the electrode when the electrode impinges upon a tissue surface.

* * * * *